United States Patent [19]

Sauter

[11] Patent Number: 6,039,700
[45] Date of Patent: *Mar. 21, 2000

[54] DOCKING ASSEMBLY FOR THE EXTENSION OF A GUIDEWIRE

[75] Inventor: Herbert Sauter, Winkel-Rüti, Switzerland

[73] Assignee: Schneider (Europe) A.G., Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/764,531

[22] Filed: Dec. 12, 1996

[30] Foreign Application Priority Data

Jun. 25, 1996 [EP] European Pat. Off. ............. 96110222

[51] Int. Cl.$^7$ ....................................................... A61B 5/00
[52] U.S. Cl. ........................................... 600/585; 600/434
[58] Field of Search ..................... 128/656, 657, 128/658, 772; 403/306, 307, 343; 411/424, 426; 600/433, 434, 435, 585

[56] References Cited

U.S. PATENT DOCUMENTS

| Re. 34,466 | 12/1993 | Taylor et al. | 128/657 |
|---|---|---|---|
| 750,343 | 1/1904 | Brockway | 403/343 |
| 1,879,856 | 9/1932 | Peterson | 403/343 |
| 2,024,982 | 12/1935 | Scott | 128/349 |
| 4,003,369 | 1/1977 | Heilman et al. | 128/2 |
| 4,724,846 | 2/1988 | Evans, III | 128/772 |
| 4,779,628 | 10/1988 | Machek | 128/772 |
| 4,827,941 | 5/1989 | Taylor et al. | 128/657 |
| 4,846,193 | 7/1989 | Tremulis et al. | 128/772 |
| 4,854,330 | 8/1989 | Evans, III et al. | 128/772 |
| 4,895,168 | 1/1990 | Machek | 128/772 |
| 4,917,103 | 4/1990 | Gambale et al. | 128/772 |
| 4,922,923 | 5/1990 | Gambale et al. | 128/772 |
| 4,958,642 | 9/1990 | Christian et al. | 128/772 |
| 4,966,163 | 10/1990 | Kraus et al. | 128/772 |
| 5,031,636 | 7/1991 | Gambale et al. | 128/772 |
| 5,083,935 | 1/1992 | Herman | 439/433 |
| 5,109,867 | 5/1992 | Twyford et al. | 128/772 |
| 5,113,872 | 5/1992 | Jahrmarkt et al. | 128/772 |
| 5,117,838 | 6/1992 | Palmer et al. | 128/772 |
| 5,127,917 | 7/1992 | Niederhauser et al. | 606/191 |
| 5,131,204 | 7/1992 | Hiendl | 52/726 |
| 5,139,032 | 8/1992 | Jahrmarkt et al. | 128/772 |
| 5,169,183 | 12/1992 | Hallez | 285/334 |
| 5,188,621 | 2/1993 | Samson | 604/283 |
| 5,191,888 | 3/1993 | Palmer et al. | 128/657 |
| 5,195,535 | 3/1993 | Shank | 128/772 |
| 5,197,486 | 3/1993 | Frassica | 128/772 |
| 5,217,026 | 6/1993 | Stoy et al. | 128/772 |
| 5,234,002 | 8/1993 | Chan | 128/772 |

(List continued on next page.)

FOREIGN PATENT DOCUMENTS

| 0315941A3 | 5/1988 | European Pat. Off. . |
|---|---|---|
| 0321796A2 | 6/1989 | European Pat. Off. . |
| 0383159A1 | 8/1990 | European Pat. Off. . |
| 0442044A1 | 8/1991 | European Pat. Off. . |
| 2305039 | 10/1976 | France . |
| 3816638A1 | 12/1988 | Germany . |
| 9218051 | 10/1992 | WIPO . |
| 9303664 | 3/1993 | WIPO . |
| 9314805 | 8/1993 | WIPO . |

OTHER PUBLICATIONS

European Search Report in corresponding European Patent Application No. 96110222.5, together with communication and one page Annex.

*Primary Examiner*—Charles Marmor, II
*Attorney, Agent, or Firm*—Crompton, Seager & Tufte, LLC

[57] ABSTRACT

A plug and socket assembly for the extension of a guidewire with an extension wire. The plug is formed at the distal end of the extension wire and the socket is formed at the proximal end of the guidewire. Inside the socket is a female conical screw thread and outside the plug is a conical male screw thread. Assembly is obtained by mere insertion and screwing of conical male screw thread into conical female screw thread.

3 Claims, 3 Drawing Sheets

U.S. PATENT DOCUMENTS

| | | | |
|---|---|---|---|
| 5,247,942 | 9/1993 | Prather et al. | 128/772 |
| 5,271,415 | 12/1993 | Foerster et al. | 128/772 |
| 5,275,173 | 1/1994 | Samson et al. | 128/772 |
| 5,282,478 | 2/1994 | Fleischhaker et al. | 128/772 |
| 5,295,492 | 3/1994 | Sellers | 128/772 |
| 5,339,833 | 8/1994 | Berthiaume et al. | 128/772 |
| 5,341,818 | 8/1994 | Abrams et al. | 600/585 |
| 5,361,777 | 11/1994 | Sellers | 128/772 |
| 5,365,943 | 11/1994 | Jansen | 600/585 |
| 5,404,886 | 4/1995 | Vance | 128/772 |
| 5,415,178 | 5/1995 | Hsi et al. | 128/772 |
| 5,421,348 | 6/1995 | Larnard | 128/772 |
| 5,429,139 | 7/1995 | Sauter | 128/772 |
| 5,441,055 | 8/1995 | Ales et al. | 128/772 |
| 5,497,782 | 3/1996 | Fugoso | 128/772 |
| 5,511,559 | 4/1996 | Vance | 128/772 |
| 5,513,650 | 5/1996 | Johansen | 128/772 |
| 5,527,298 | 6/1996 | Vance et al. | 604/280 |
| 5,546,958 | 8/1996 | Thorud et al. | 128/772 |
| 5,555,893 | 9/1996 | Hackett et al. | 128/772 |
| 5,605,163 | 2/1997 | Hani | 128/772 |
| 5,617,875 | 4/1997 | Schwager | 128/772 |

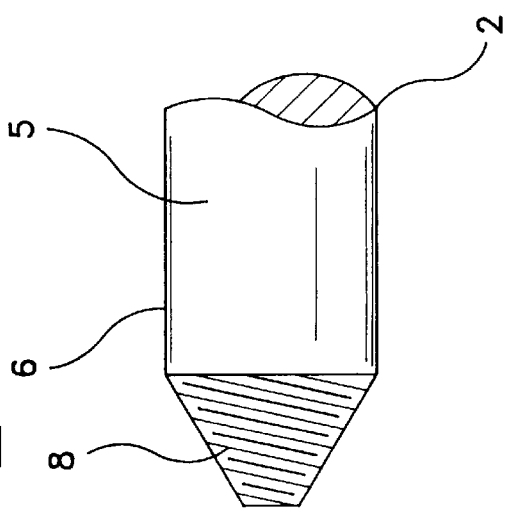
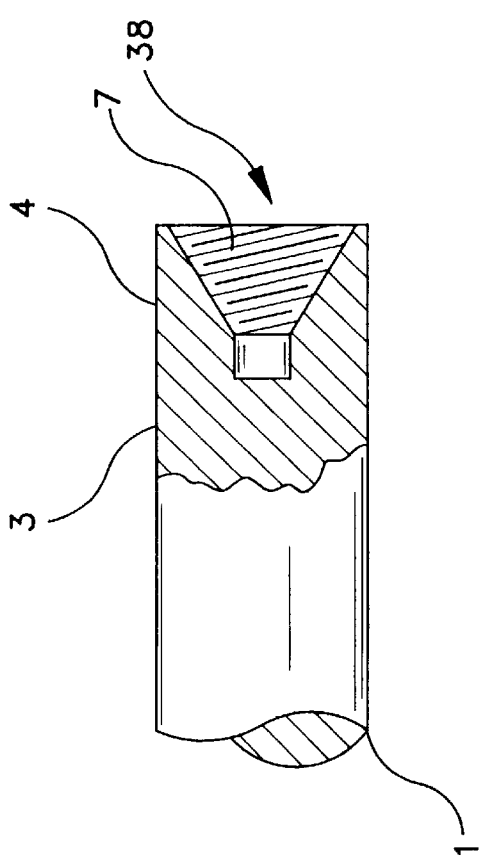
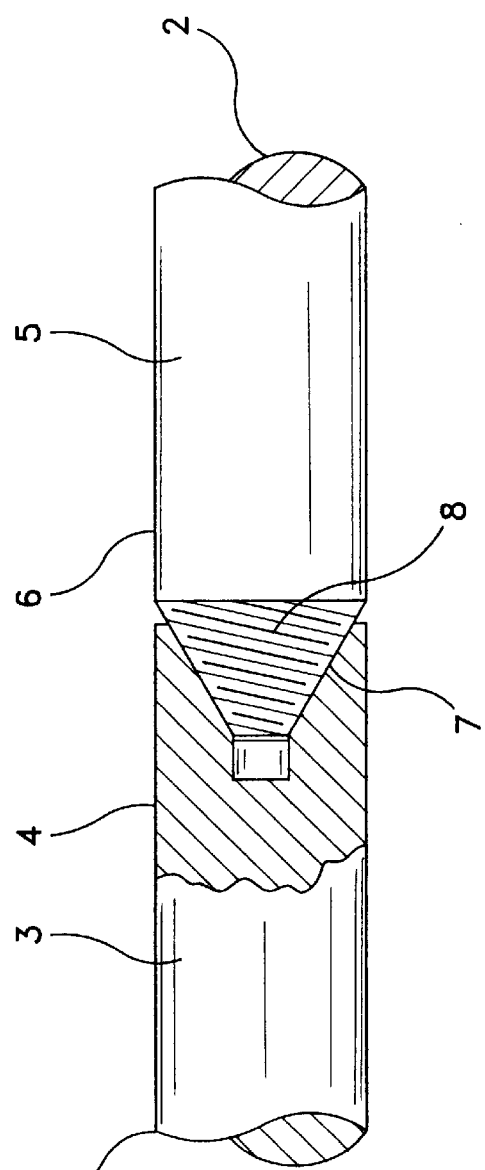

DOCKING ASSEMBLY FOR THE EXTENSION OF A GUIDEWIRE

BACKGROUND OF THE INVENTION

This invention relates to a docking assembly for the extension of a guidewire with an extension wire.

It is common practice to use a guidewire for the placement of a catheter in vascular procedures such as percutaneous transluminal cardiovascular angioplasty. A guidewire typically is slightly longer than the catheter with which it is used, whereby a relatively short portion of the guidewire protrudes proximally from the catheter when the catheter is in place. If it becomes necessary to exchange the catheter, for example to increase the balloon size in an angioplasty procedure, the guidewire must be removed and replaced by an exchange wire which is about twice the length of the catheter in order to allow withdrawal of the catheter and insertion of a new catheter over the exchange wire. However, this procedure substantially complicates and slows down the vascular treatment, and there has been several attempts to attach an extension wire to the initial guidewire in order to avoid the need of exchange of the guidewire.

A docking assembly as generally described hereinabove is shown in the document EP 0 383 159 A1, in which an extendable guidewire system for vascular procedures comprises a main section with a threaded male portion at its proximal end, and an extension section which has a female connection member comprising an internal thread at its distal end and a collar at its proximal end. This female connection member is mounted on a ball configuration arranged at the distal end of the extension section, the ball configuration being located between the collar of the female connection and the internal thread, thereby assuring to the female connection a free rotation capacity. Accordingly, connection of the assembly is achieved by manually threading the rotatable female member on the male member, and disconnection is obtained by the reverse, which is easy because of the ball mounting of the female member. However, this configuration requires several turns to assure a relatively safe connection. Furthermore, the ball mounted thread connection has no self-locking capacity, whereby the risk of having the connection getting loose due to the manipulations of the guidewire during the vascular procedure.

A further docking assembly directed to a similar environment is described in U.S. Pat. No. 5,234,002 which shows a catheter exchange system in which the proximal end of a guidewire is provided with male threads and the distal end of an extension wire has a tubular member with internal female threads for meshing with the male threads of the guidewire. A connecting member forming a cylinder with an inner lumen extending therethrough is adapted to frictionally engage and secure the tubular member of the extension wire so that rotation of the connecting member causes rotation of the extension wire. The connecting member has a longitudinal slit provided through its wall and a flared entry to accommodate the proximal end of the guidewire. Connection is obtained by engaging the connecting member over the proximal end of the guidewire and rotating it to ensure meshing of the female threads at the distal end of the extension wire with the male threads at the proximal end of the guidewire. Complete engagement of the female threads over the male threads is indicated by sliding rotation of the connecting member with respect to the tubular member. Then, the connecting member must be removed and the slit thereof allows separation from the tubular member by peeling the connecting member off the tubular member. To disconnect the assembly, the extension wire must be twisted to disengage the threaded connection between it and the guidewire. This system also requires several turns to assure a relatively safe connection, however, with the additional drawback that the extension wire will be considerably twisted, hence a strong potential of getting it entangled and damaged. Furthermore, this thread connection also has no self-locking capacity; accordingly, either the assembly must be completely screwed until blocking up against some end of stroke structure or abutment, with the resulting increase in the twisting of the extension wire, or one has to accept the risk of having the connection getting loose due to manipulations of the guidewire during a vascular procedure. And removal of the connecting member by peeling it off the tubular member of the extension wire may prove difficult and delicate.

Still in a similar environment, the document WO 93/03664 shows an extendable guidewire system in which the proximal end of a guidewire is terminated by a helical coil partially loosely wound to provide gaps between adjacent coil turns, and the distal end of an extension wire is also terminated by a helical coil partially loose to provide gaps between adjacent coil turns. These coils are for alignment and rotation with respect to each other so that the respective spaced coils engage into each other. A swivel mounting of the helical coils may prevent twisting of the guidewire or extension wire. As the aligned coil engagement may easily jam in case of misalignment of the helical coils, a further embodiment provides for a guiding pin affixed to the extension wire within the corresponding helical coil, this guiding pin being dimensioned to fit inside the helical coil of the guidewire. This solution leads however to a deadlock: if the guiding pin does not fit relatively tightly within the helical coils, the connection has some flexibility, but the coils have a serious potential of jam; and if the guiding pin fits relatively tightly within the helical coils, the risk of jam is reduced, but the connection becomes rigid all along the engagement of the helical coils. And as the system has no intrinsic self-locking capacity, there remains the risk of having the connection getting loose at some moment of the vascular procedure.

Other arrangements are available. For example, the document WO 93/14805 shows a guidewire extension system comprising a turnbuckle nut formed by a tubular body in which are affixed a right-handed helically wound wire and a left-handed helically wound wire respectively defining a right-handed helical groove and a left-handed helical groove. The proximal end of the guidewire and the distal end of the extension wire are both tapered and each have a flattened tip for engagement into the grooves of the turnbuckle nut. For assembly, the flattened tips of the extension wire and guidewire are respectively engaged into the ends of the turnbuckle nut which is then rotated to cause the flattened tips to pass respectively along the left-handed helical groove and right-handed helical groove. Thus, the flattened tips of the guidewire and extension wire will meet at the ends of the helical right-handed and left-handed grooves. To disassemble the guidewire and extension wire, the turnbuckle nut must be rotated in the opposite direction in order to cause the flattened tips of the guidewire and extension wire to pass along the corresponding helical grooves until they are expelled out of the turnbuckle nut. This assembly assures a twist free connection, however, it requires a plurality of turns of the turnbuckle nut for connection and disconnection. And as it has no intrinsic self-locking capacity, it is necessary to fully wind both the tips of the guidewire and extension wire until they meet each other to achieve some friction contact between them, or to arrange for some frictional contact between the guidewire, the extension wire and the turnbuckle end edges to achieve a locking of the assembly and avoid its getting loose during a vascular procedure. Apart of this, the system does not easily permit a two-hand operation because of the need to master three elements simultaneously, whereof the need to have more people than advisable around the operating table. As a variant, the turnbuckle nut may be crimped to the distal end of the extension wire while retaining its basic function. This may facilitate a two-hand operation, however, the crimp must be precisely located in a manner allowing sufficient longitudinal play of the turnbuckle nut before groove engagement of the distal end of the extension wire in order to avoid the risk of having the proximal end of the guidewire insufficiently engaged in its corresponding groove to assure a safe connection via the turnbuckle function. This may involve complications for the expected two-hand operation.

U.S. Pat. No. 5,117,838 shows a guidewire extension system comprising an extension guidewire adapted to be releasably connected to a ground down proximal end of a guidewire. The distal end of the extension wire is mounted in a tube in which is located an open pitch flat wire coiled spring, one end of which is welded over the distal end of the extension wire, whereas the other end of the coiled spring extends freely in the tube where an end detent prevents the free end of the coiled spring to be moved out of the tube. To facilitate handling, an alignment tool in the form of a cylindrical structure with flared entries is intended to receive the tube in one end and the proximal end of the initial guidewire at the other end. To achieve connection, the ground down end of the guidewire and the tube of the extension wire are inserted into the alignment tool and the ground down end of the guidewire is pushed into the tube and urged therein until it engages the coiled flat wire spring and bottoms against the corresponding end of the extension wire. As the ground down end of the guidewire is inserted into the coils of the flat wire spring, the coils are forced to slightly uncoil and then, any axial force pulling the end of the guidewire away from the coiled spring causes its coils to move towards a smaller diameter which establishes a connection between the coils and the ground down end of the guidewire. To disconnect the assembly, it is necessary to rotate the extension wire in order to loosen the grip of the coiled spring against the ground down end of the guidewire and at the same time to pull the latter out of engagement with the coils of the spring. This assembly provides a self-locking connection which is however dependent on manipulations and skills to be disconnected and on an alignment tool for connection. To minimize the twisting of the extension wire for disconnection purposes, a further embodiment provides for swivel mounting of the tube containing the flat wire coiled spring. This configuration has, however, the disadvantage of an added mechanical complication with the risk of having the swivel tube clogging on the distal end of the extension wire.

U.S. Pat. No. 5,197,486 shows a detachable guidewire extension system in which the proximal end of the guidewire is provided with a reduced diameter rod adapted to mate with a connector socket attached to the distal end of an extension wire. This connector socket has a tubular housing containing a helical coil attached at its proximal end to the proximal end of the housing and it has an outer diameter slightly less than the inner diameter of the housing which has an inward circular lip at its distal end to prevent extension of the helical coil out of the housing. The inner diameter of the coil is less than the outer diameter of the rod at the proximal end of the guidewire. Connection of the system is achieved by urging the rod into the housing to cause the coil to expand to receive the rod. A slight rotation of the extension wire may facilitate insertion of the rod into the coil. To disconnect the assembly, it is necessary to rotate the extension wire while holding the guidewire to relax the grip of the coil on the rod and to separate the guidewire and extension wire while doing so. This is substantially the same operation as in the first embodiment of U.S. Pat. No. 5,117,838 described hereinbefore. As with this configuration, there is a self-locking connection which is dependent on manipulations and skills to be disconnected, in particular because of the need to rotate the extension wire while pulling it out of the housing.

U.S. Pat. No. 5,109,867 shows extendable guidewire assemblies comprising axial interlocking members respectively fastened to corresponding ends of the guidewire and guidewire extension, and a retractable spring biased sleeve which has to be retracted to permit the interlocking members to be interlocked, which sleeve has then to be extended to enclose the interlocked members in order to maintain them in interlocked conditions. To lock the assembly, it is therefore necessary to first retract the sleeve to fully free one of the interlocking members, then to place another interlocking member in interlocking condition with respect to the first interlocking member, and finally to allow the spring biased sleeve to move over the interlocked members to maintain the interlocked assembly. To unlock the system, it is sufficient to retract the sleeve up to freeing both the interlocking members in order to separate them. The system is shown in various embodiments in which the interlocking is obtained by overlapping two coiled members, or by inserting a ball into expandable tongues, or by overlapping hook-like members, or still by inserting a cylindrical head into a slotted bore. Apart from the multiplicity of elements which may clog or jam, these interlocking systems may prove difficult to operate because of the need to retract the spring biased sleeve for interlocking the interlocking members. A two-hand operation may be therefore hazardous, which may result in the need of having more people than otherwise needed around the patient.

U.S. Pat. No. 5,195,535 is directed to a connection system for a guidewire and guidewire extension in which the proximal end of the guidewire is terminated by a socket whereas the distal end of the guidewire extension comprises a wire having a reduced diameter end portion carrying a movable sleeve. A wedging element is affixed to the tip of the reduced diameter end portion of the wire, and a tubular handle is affixed by its distal end to the proximal end of the movable sleeve. To achieve connection, the sleeve is first withdrawn proximally over the extension wire by pulling proximally the tubular handle while maintaining or pushing the extension wire and its wedging element. The wire and sleeve are then inserted into the socket of the guidewire by pushing distally the wire and handle simultaneously. Then, holding the handle to maintain the position of the sleeve in the socket, the extension wire is pulled proximally to cause the wedging element to engage and become firmly wedged in the distal end of the sleeve. Further advancement of the wedging element in the sleeve causes the sleeve to expand radially into engagement with the inner wall of the socket, thereby assuring gripping of the sleeve in the socket. To disconnect the assembly, it is necessary to forcibly pull proximally the handle to proximally draw the sleeve out of its wedged condition between the inner surface of the socket and the wedging element. Though relatively complicated on a structural viewpoint, the system provides a strong and safe connection between guidewire and extension wire. However, it needs skills to properly connect and release the assembly. Furthermore, it does not practically permit a two-hand operation, being necessary to manipulate the handle, the extension wire, and the socket of the guidewire, whereby the need of more people than normally required around the patient.

It is an object of this invention to improve the conditions of attaching an extension wire to a guidewire and to avoid the aforesaid drawbacks. It is a further object of the invention to achieve attachment and release of a guidewire and extension wire by means of a docking assembly which is simple and advantageous to manufacture, which guarantees an efficient and safely repetitive operation for both connection and release of the assembly, which does not require skills or tooling manipulations, which is not influenced by slippery fluids and other clogging agents, and which is positive and highly versatile.

All documents cited herein, including the foregoing, are incorporated herein by reference in their entireties for all purposes.

SUMMARY OF THE INVENTION

To this effect, the docking assembly according to the invention may include socket means formed at a mating end of one of the guidewire and extension wire, plug means formed at a mating end of the other of the guidewire and extension wire, and meshing means for releasably connecting the plug means with the socket means.

Accordingly, where the meshing means comprise conical helically wound rib means formed on one of the socket and plug means, and means formed on the other of the socket and plug means for a threadlike engagement with the conical helically wound rib means, an extremely fast, effortless, easy and safe connection of the system is achieved because of the practically immediate locking resulting from the conical threadlike assembly. Due to its intrinsic geometry, the conical threadlike assembly is fully positive and self-locking and there is no risk of having the connection getting loose during a vascular procedure. No particular orientation or precise positioning is required for introduction of the plug and socket means of the guidewire and extension wire into each other. The very small turning angle resulting from the conical threadlike assembly results in a negligible twisting of the guidewire and/or extension wire. Fewest manipulations, no assembly tools and no skills are required to merely insert the plug and socket means into each other and slightly turn them to directly lock them. Unlocking is as fast and easy. The system requires a very small number of integers, the assembly being limited to the conical helically wound rib means and the means for a threadlike engagement therewith. As the conical threadlike assembly requires a very short turning angle to secure a positive locking, the connection is longitudinally short, whereby the influence of the rigidity of the connection on the flexibility of the junction between guidewire and extension wire is practically negligible. And as it has a little dependency on the diametrical size of the guidewire and extension wire, it allows the extension of guidewires with differing diameters so that an extension wire can be used and consequently stored to serve as an extension for different guidewires.

Within this environment, the versatility of the system allows a number of various configurations without losing its advantages.

For example, the conical helically wound rib means may comprise a conical male screw thread formed on the plug means; alternatively, the conical helically wound rib means may comprise a conical coil arranged on the plug means. The means for a threadlike engagement with the conical helically wound rib means may comprise a conical female screw thread formed in the socket means; alternatively, the means for a threadlike engagement with the conical helically wound rib means may comprise a conical coil formed in the socket means. Still, the means for a threadlike engagement with the conical helically wound rib means may comprise ring means fastened in the socket means; advantageously, such ring means comprise an inner circular ridge. It is readily apparent that where the conical helically wound rib means comprise a conical male screw thread formed on the plug means, this configuration may be used with either of the configurations forming the means for a threadlike engagement with the conical helically wound rib means, namely, the conical female screw thread, or the conical coil, or still the ring means, possibly with an inner circular ridge, arranged in the socket means. Similarly, it is readily apparent that where the conical helically wound rib means comprise a conical coil arranged on the plug means, this structure may be used with either of the structures forming the means for a threadlike engagement with the conical helically wound rib means, namely, the conical female screw thread, or the conical coil or still the ring means with or without an inner circular ridge, arranged in the socket means.

Still a further embodiment may provide for the conical helically wound rib means being formed in the socket means, wherein the plug means comprise ring means formed thereon for threadlike engagement with the conical helically wound rib means; advantageously the ring means comprise an outer circular ridge. And it is also apparent that the ring means configuration, with or without outer circular ridge, may be used with either of the structures forming the conical helically wound rib means, namely, the conical female screw thread or the conical coil.

In sum, the present invention relates to a docking assembly for the extension of a guidewire with an extension wire including socket means formed at a mating end of one of the guidewire and extension wire, plug means formed at a mating end of the other of the guidewire and extension wire, and meshing means for releasably connecting the plug means with the socket means, wherein the meshing means include conical helically wound rib means formed on one of the socket and plug means, and means formed on the other of the socket and plug means for a threadlike engagement with the conical helically wound rib means. The conical helically wound rib means may include a conical male screw thread formed on the plug means. The conical helically wound rib means may include a conical coil arranged on the plug means. The means for a threadlike engagement with the conical helically wound rib means may include a conical female screw thread formed in the socket means. The means for a threadlike engagement with the conical helically wound rib means may include a conical coil formed in the socket means. The means for a threadlike engagement with the conical helically wound rib means may include a ring means fastened in the socket means. The ring means may include an inner circular ridge. The conical helically wound rib means may be formed in the socket means, and the plug means may include ring means formed thereon for threadlike engagement with the conical helically wound rib means. The ring means may include an outer circular ridge. The conical helically wound rib means may include a conical female screw thread. The conical helically wound rib means may include a conical coil.

These and other objects, features and advantages of the invention will become readily apparent from the following detailed description with reference to the accompanying drawings which show, diagrammatically and by way of example only, preferred but still illustrative embodiments of the invention.

As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTION OF THE DRAWINGS

FIG. 1 is a longitudinal part sectional view of a first embodiment of the socket means.

FIG. 2 is a longitudinal part sectional view of a first embodiment of the plug means.

FIG. 3 is a longitudinal part sectional view showing the assembly of the elements of FIGS. 1 and 2.

DETAILED DESCRIPTION OF THE INVENTION

Figure 4:
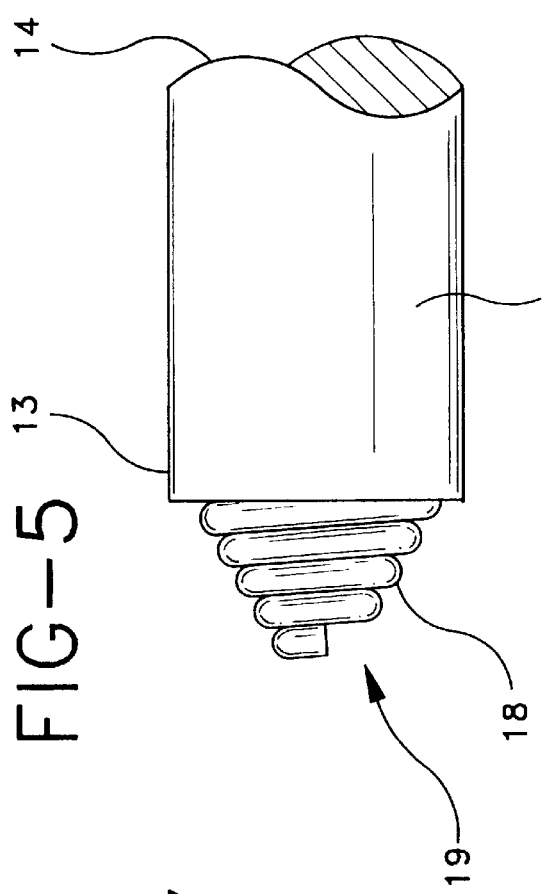
FIG. 4 is a longitudinal part sectional view of a second embodiment of the socket means.

The docking assembly shown in FIGS. 1–3 is for the extension of a guidewire 1 with an extension wire 2, both partly shown.

This docking assembly comprises a socket 3 formed at the proximal end 4 of the guidewire 1, and a plug 5 formed at the distal end 6 of the extension wire 2.

Inside the socket 3 is a conical female screw thread 7 the flare 38 of which is directed outwardly of the proximal end 4 of the guidewire 1.

Outside the plug 5 is a conical male screw thread 8 the conicity of which is distally oriented with respect to the extension wire 2.

As shown in FIG. 3, the plug 5 and socket 3 are assembled by mere insertion and screwing of conical male thread 8 into conical female screw thread 7. Disassembly is obtained by the reverse.

Figure 5:
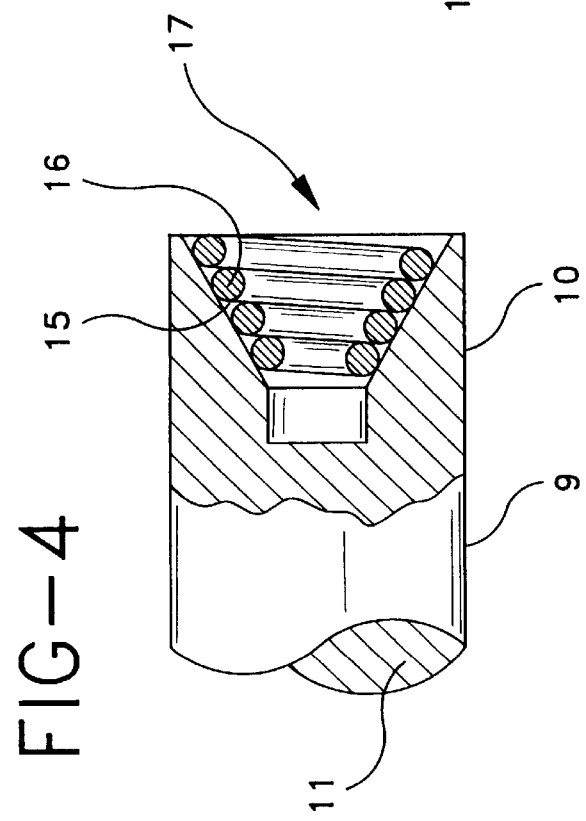
FIG. 5 is a longitudinal view of a second embodiment of the plug means.

FIGS. 4 and 5 show a second embodiment of the plug and socket configuration.

The socket 9 is also formed at the proximal end 10 of the guidewire 11, whereas the plug 12 is formed at the distal end 13 of extension wire 14.

In a conical recess 15 at the proximal end 10 of socket 9 is affixed, for example glued, a conical coil 16 the flare 17 of which is directed outwardly of the proximal end 10 of guidewire 11.

At the distal end 13 of extension wire 14 is affixed, for example welded or glued, a conical coil 18 the conicity 19 of which is oriented distally of the extension wire 14.

Assembly of plug 12 and socket 9 is achieved as in the embodiment of FIGS. 1–3 by mere insertion and screwing of conical coil 18 of plug 12 into conical coil 16 of socket 9. Disassembly is also obtained by the reverse.

Figure 7:
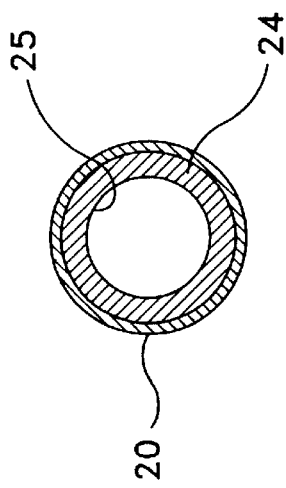
FIG. 7 is a view according to line VII—VII of FIG. 6.
Figure 6:
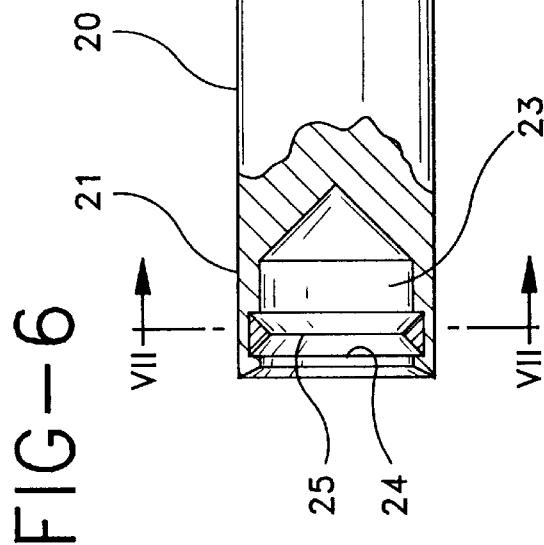
FIG. 6 is a longitudinal part sectional view of a third embodiment of the socket means.

In FIGS. 6 and 7 there is shown a third embodiment of the socket. In this embodiment also, the socket 20 is formed at the proximal end 21 of the guidewire 22.

The socket 20 comprises a recess 23 in which is fastened, for example glued, a ring 24 having an inner circular ridge 25. The plug, not shown, may be either as shown in FIG. 2 or as shown in FIG. 5, whereas assembly is obtained by mere insertion and screwing of the plug into the ring 24 the inner ridge 25 of which will threadlike engage the conical male thread of FIG. 2 or the conical coil of FIG. 5.

Figure 9:
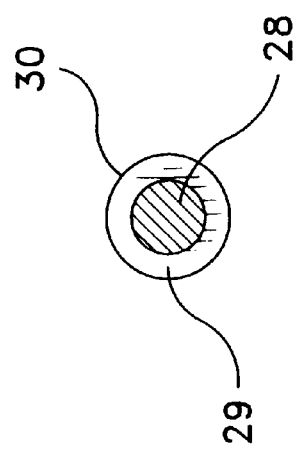
FIG. 9 is a view according to line IX—IX of FIG. 8.
Figure 8:
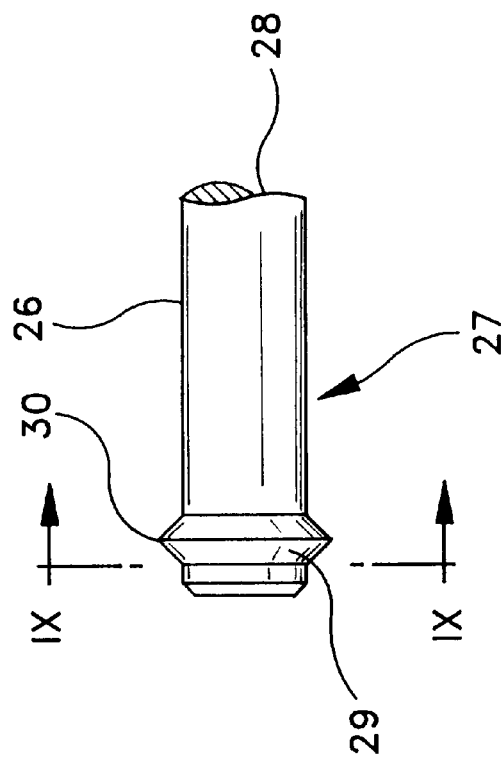
FIG. 8 is a longitudinal view of a third embodiment of the plug means.

FIGS. 8 and 9 show a third embodiment of the plug. In this embodiment, the plug 26 is formed at the proximal end 27 of guidewire 28.

The plug 26 comprises a transverse ring 29 having an outer circular ridge 30. The socket, not shown, may be either as shown in FIG. 1 or in FIG. 4 and mounted on the distal end of the extension wire (not shown); accordingly, assembly of plug and socket is obtained by merely inserting and screwing the ring 29 of plug 26 into the socket, whereas the outer ridge 30 of ring 29 will threadlike engage with the conical female screw thread of FIG. 1 or the conical coil of FIG. 4.

Accordingly, in all the embodiments shown, the assembly of guidewire and extension wire is obtained by the meshing of conical helically wound rib means and means for a threadlike engagement with the conical helically wound rib means.

Variants may be envisaged without departing from the scope of the invention. For example, the plug and socket mounting on the guidewire and extension wire may be reversed, that is to say where the plug has been shown on the extension wire and the socket on the guidewire, the contrary is readily available; and the situation is the same where the plug has been shown on the guidewire (FIGS. 9 and 10). Although the outer diameter of both the plug and socket of FIGS. 1–3 are substantially the same, such diameters may differ from one another.

It will be evident from considerations of the foregoing that the Docking Assembly for the Extension of a Guidewire may be constructed using a number of methods, in a wide variety of sizes and styles for the greater efficiency and convenience of a user. The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A guidewire extension system, comprising:

a flexible guidewire having a distal end, a proximal end, and a conical female screw thread disposed proximate the proximal end thereof;

a flexible extension wire having a distal end, a proximal end, and a conical male screw thread disposed proximate the distal end thereof; and the conical male screw thread being adapted to releasably mate with the conical female screw thread to form a temporary connection between the proximal end of the guidewire and the distal end of the extension wire.

2. A guidewire extension system including an extension wire releasably joined to a guidewire, the guidewire extension system comprising:

the guidewire having a distal end, a proximal end, and a conical female screw thread disposed proximate the proximal end thereof;

the extension wire having a distal end, a proximal end, and a conical male screw thread disposed proximate the distal end thereof;

wherein, the conical male screw thread is disposed within the conical female screw threads; and the conical male screw thread being releasably intermeshed with the conical female screw thread to form a releasable connection between the proximal end of the guidewire and the distal end of the extension wire.

3. A method of releasably joining an extension wire to a guidewire comprising the steps of:

providing a flexible guidewire having a distal end, a proximal end, and a conical female screw thread disposed proximate the proximal end thereof;

providing a flexible extension wire having a distal end, a proximal end, and a conical male screw thread disposed proximate the distal end thereof;

positioning the distal end of the extension wire proximate the proximal end of the guidewire;

advancing the conical male screw thread into the conical female screw thread;

rotating the extension wire by a turning angle which is sufficient to releasably intermesh the conical male screw thread of the extension wire with the conical female screw thread of the guidewire to form a releasable and temporary connection between the proximal end of the guidewire and the distal end of the extension wire.

* * * * *